United States Patent [19]

Holm

[11] Patent Number: 4,605,777

[45] Date of Patent: Aug. 12, 1986

[54] METHOD OF MANUFACTURING O- AND P-NITROBENZALDEHYDE

[75] Inventor: Boris Holm, Karlskoga, Sweden

[73] Assignee: Nobel Kemi AB, Karlskoga, Sweden

[21] Appl. No.: 744,143

[22] Filed: Jun. 12, 1985

[30] Foreign Application Priority Data

Jun. 13, 1984 [SE] Sweden ................................ 8403147

[51] Int. Cl.$^4$ ............................................. C07C 79/36
[52] U.S. Cl. .................................................. 568/424
[58] Field of Search ........................................ 568/424

[56] References Cited

U.S. PATENT DOCUMENTS 4,203,928  5/1980  Meyer .................................. 568/424
4,297,519  10/1981 Ertel .................................... 568/424
4,463,195  7/1984  Marti et al. ......................... 568/424

OTHER PUBLICATIONS

Hilgetag et al., Preparative Organic Chemistry (1972), 475–477.

Primary Examiner—Bernard Helfin
Attorney, Agent, or Firm—Pollock, Vande Sande & Priddy

[57] ABSTRACT

This invention relates to a method of manufacturing ortho- and para-nitrobenzaldehyde from o-chloro or o-bromobenzaldehyde and p-chloro or p-bromobenzaldehyde respectively through a nucleophilic aromatic substitution reaction performed in an organic solvent.

11 Claims, No Drawings

METHOD OF MANUFACTURING O- AND P-NITROBENZALDEHYDE

This invention relates to a method of manufacturing o- and p-nitrobenzaldehyde from o-chloro or o-bromobenzaldehyde and p-chloro- or p-bromobenzaldehyde respectively.

At present these compounds which are used as intermediates in, among other things, the manufacture of drugs, are manufactured in accordance with relatively elaborate methods and for this reason command a high price per kilogram. The manufacture of m-nitrobenzaldehyde, in contrast, is less problematical since this compound can be attained through simple nitration of benzaldehyde.

A large number of more or less complicated ways of synthesis for the manufacture of o-nitrobenzaldehyde are previously known. The method that is probably most widely known is the one involving an oxidation of o-nitrotoluene with chromic acid in acetic acid anhydride. With regard to the actual reaction, this method does not involve any major problems and the various reagents have a reasonable market price. On the other hand, the method gives such serious waste problems with the chromium salts formed as residual products in the reaction that the method nowadays has been more or less completely abandoned.

It is further known that o-nitrobenzaldehyde can be produced in different ways from o-nitrobenzoyl chloride or o-nitrobenzal bromide but both of the starting materials are in themselves so difficult to obtain that this synthesis method has not become particularly common.

Another method of synthesis for the manufacture of o-nitrobenzaldehyde which on account of the low yield has proved to be technically completely uninteresting is to perform a side chain nitration of ortho-nitrotoluene with a subsequent oxidation with potassium permanganate of the intermediate produced in the initial reaction.

o-nitrobenzaldehyde can also be manufactured from o-nitrobenzoyl bromide via a modified Kröhnke reaction. This method, however, has very little technical appeal since it requires both expensive and carcinogenic additives.

A method has also been proposed for the manufacture of o-nitrobenzaldehyde by conversion of o-nitrotoluene with a suitable oxalic acid diester containing a lower alkyl or aryl group and subsequently converting the then obtained alkaline salt of o-nitrophenylepyruvic acid into o-nitrobenzylidene chloride through addition of alkali hypochlorite, and then finally hydrolizing the thus obtained o-nitrobenzylidene chloride into o-nitrobenzaldehyde. This method, however, is relatively elaborate and therefore not very attractive.

Also previously known are a few further methods for the manufacture of o-nitrobenzaldehyde but all of them give such low yields that they are of no interest for the technical production of the product in question.

The state of the art technology also includes, however, another proposal for the manufacture of p-nitrobenzaldehyde through oxidation of p-nitrotoluene with ozone in a solution of acetic acid and acetic acid anhydride in the presence of a metal bromide catalyst. Normally, the oxidation of p-nitrotoluene would give p-nitrobenzoic acid via p-nitrobenzaldehyde but through the acetic acid anhydride additive it is asserted that the oxidation can be stopped at the aldehyde stage. Whether or not this method can be used for technical production of p-nitrobenzaldehyde or if it is only of more theoretical interest is nevertheless unclear.

As previously pointed out, the present invention relates to a method of manufacturing o- and p-nitrobenzaldehyde from o-chloro or o-bromobenzaldehyde and p-chloro or p-bromobenzaldehyde respectively.

According to the present invention, the chloro- and bromo-substituent of the original substance is replaced with a nitrite ion through a direct nucleophilic aromatic substitution reaction performed in an organic solvent, preferably in the presence of a catalyst.

The reactions, then, would take place in accordance with the following general formula:

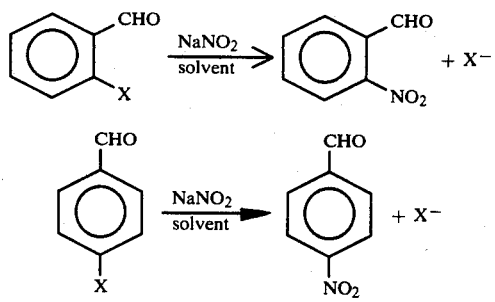

where X=Cl or Br.

Nucleophilic substitution with nitrite ions is known in halogenated aliphats and in reaction with iodonium salts for the production of nitro-aromatics. On the hand, we have been unable to establish that there is prior art knowledge that it is possible to perform direct nucleophilic aromatic substitutions of chloro- or bromo-substituents on a benzene derivative of the kind with which we are concerned in this context.

It has also been found that the result of the reaction according to the invention is clearly dependent on which organic solvent is used. Dimethylformamide thus gives a decidedly better result than other tested solvents such as N-methylpyrrolidone, nitrobenzene, polyethylene glycol, dimethylsulphoxide, sulpholan and chlorobenzene.

The nucleophilic substitution of the chloro- or bromo-substituent concerned has also proved to be dependent upon how the nitrite ion is supplied. Sodium nitrite in dimethylformamide thus gives a significantly faster reaction than potassium nitrite when it comes to reacting with chloro- or bromobenzaldehyde.

Yet another important detail in connection with the invention is that the actual substitution reaction is catalysed by the presence of a halogen copper salt such as CuI, CuBr$_2$, CuBr, CuCl$_2$ or CuCl and also by CuSO$_4$. The above mentioned halogen copper salts, however, do not only function as catalysts. The halogens from the respective copper salt will in fact also partly react with the halogen benzaldehyde. We have found that in the reaction with o-bromobenzaldehyde in the presence of CuCl or CuCl$_2$ o-chlorobenzaldehyde is also formed, which is assumed to take place in accordance with the following formula:

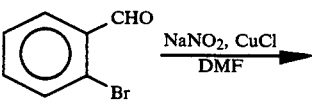

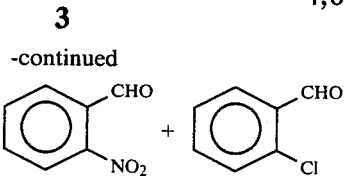

Certain other non-identified byproducts were also formed in small quantities. A corresponding reaction is obtained in the presence of copper bromide or copper iodide. During the initial phase of the reaction some development of nitrous gases can usually be noted. This indicates that a small portion of the starting material and possibly also of the produced product is oxidised. The losses then arising are, however, no greater than can be accepted without further ado. We have also found that it is difficult to continue the process until all starting material has been consumed without the produced, wanted benzaldehyde decomposing at the same time.

Attempts to perform the reaction in an autoclave at 200° C. have shown that the yield is not improved at an elevated temperature. To begin with, the reaction takes place more quickly, but the reaction product starts to be degraded through oxidation with simultaneous liberated nitrous gases even before the wanted substitution reaction has been concluded.

In general, the reaction can be carried out employing about 5 to about 50 mmol of the nitrite salt per about 3 to about 20 mmol of the chlorobenzaldehyde or bromobenzaldehyde. The amount of solvent employed is not especially critical and need only be present in amounts sufficient for the amount of reactants employed. For instance, about 9 ml of organic solvent is quite adequate for the amounts of reactants mentioned above. The amount of copper salt catalyst is usually about 10 to about 100 mg for the amounts of reactants mentioned above. The invention has been defined in the accompanying claims and will now be further described in conjunction with some relevant examples:

EXAMPLES

All the experiments were performed in the same manner. Approximately 7 mmol of the starting substance (e.g. 1.0 g o-chlorobenzaldehyde and 1.3 g o-bromobenzaldehyde respectively) was charged in a flask equipped with a magnetic stirrer and cooler. Next, 16 mmol (=1.1 g) $NaNO_2$ and 9.0 ml dimethylformamide (DMF) was added as solvent, as well as 50 mg $CuSO_4.5H_2O$ or, alternatively, 38 mg CuI as per the table.

The reaction was subsequently performed at reflux with stirring for 5 hours.

Upon completion of the reaction the produced o- and p-nitrobenzaldehyde respectively were isolated through distillation and identified by means of gas chromatography and mass spectroscopy.

OCB=o-chlorobenzaldehyde
OBB=o-bromobenzaldehyde
PCB=p-chlorobenzaldehyde
PBB=p-bromobenzaldehyde
ONB=o-nitrobenzaldehyde
PNB=p-nitrobenzaldehyde

| Aldehyde starting material | Catalyst | Yield % | Non-consumed starting material % |
|---|---|---|---|
| OCB | — | 5 | 78 |
| OCB | $CuSO_4.5H_2O$ | 11 | 77 |
| OCB | CuI | 12 | 74 |
| PCB | $CuSO_4.5H_2O$ | 17 | 76 |
| OBB | $CuSO_4.5H_2O$ | 25 | 48 |
| PBB | $CuSO_4.5H_2O$ | 5 | 57 |
| OBB | CuI | 26 | 46 |

Thus yields of about 50% were obtained calculated upon consumed starting material.

I claim:

1. Method of manufacturing o- and p-nitrobenzaldehyde from o-chloro or o-bromobenzaldehyde and p-chloro or p-bromobenzaldehyde, respectively, characterized in that the chlorine or bromine substituent of the starting substance is exchanged for a nitro group through a nucleophilic aromatic substitution reaction performed in an organic solvent with a nitrite salt selected from the group of potassium nitrite and sodium nitrite and in the presence of a copper salt as a catalyst.

2. A method according to claim 1, characterized in that the nitrite ion is supplied in the form of sodium nitrite.

3. A method according to claim 2, characterized in that the reaction is performed with the sodium nitrite dissolved in dimethylformamide.

4. A method according to claim 1, characterized in that the reaction is performed in the presence of a halogen copper salt as a catalyst.

5. A method according to claim 2, characterized in that the reaction is performed in the presence of a halogen copper salt as a catalyst.

6. A method according to claim 3, characterized in that the reaction is performed in the presence of a halogen copper salt as a catalyst.

7. A method according to claim 1, characterized in that the reaction is performed in the presence of copper sulphate as a catalyst.

8. A method according to claim 2, characterized in that the reaction is performed in the presence of copper sulphate as a catalyst.

9. A method according to claim 3, characterized in that the reaction is performed in the presence of copper sulphate as a catalyst.

10. The method of claim 1 wherein the amount of said nitrate salt is about 5 to about 50 mmol per about 3 to about 20 mmol of the starting substance.

11. The method of claim 10 wherein the amount of copper salt catalyst is about 10 to about 100 mg.